United States Patent [19]

Hatton et al.

[11] Patent Number: 4,779,978
[45] Date of Patent: Oct. 25, 1988

[54] METHOD OF MEASURING THE REFRACTIVE INDEX PROFILE OF OPTICAL FIBERS

[75] Inventors: William H. Hatton; Eric L. Buckland, both of Raleigh; Masayuki Nishimura, Durham, all of N.C.

[73] Assignee: Sumitomo Electric Research Triangle, Inc., Research Triangle Park, N.C.

[21] Appl. No.: 904,989

[22] Filed: Sep. 8, 1986

[51] Int. Cl.[4] .................... G01N 21/41; G01N 21/84
[52] U.S. Cl. .................... 356/73.1; 356/128
[58] Field of Search .................... 356/73.1, 128

[56] References Cited

U.S. PATENT DOCUMENTS

| | | | |
|---|---|---|---|
| 4,181,433 | 1/1980 | Marcuse | 356/73.1 |
| 4,349,276 | 9/1982 | Di Vita | 356/73.1 |
| 4,361,402 | 11/1982 | Costa | 356/73.1 |
| 4,362,943 | 12/1982 | Presby | 356/73.1 X |
| 4,391,516 | 7/1983 | Boggs et al. | 356/73.1 |
| 4,441,811 | 4/1984 | Melezoglu et al. | 356/73.1 X |
| 4,468,118 | 8/1984 | Bice | 356/73.1 |
| 4,519,704 | 5/1985 | Mansfield et al. | 356/73.1 |
| 4,551,020 | 11/1985 | Reid et al. | 356/73.1 |
| 4,565,449 | 1/1986 | Grego | 356/73.1 X |
| 4,572,665 | 2/1986 | Benoit | 356/73.1 |
| 4,662,743 | 5/1987 | Nishimura et al. | 356/73.1 |

FOREIGN PATENT DOCUMENTS

| | | | |
|---|---|---|---|
| 54-35757 | 3/1979 | Japan | 356/73.1 |
| 54-35759 | 3/1979 | Japan | 356/73.1 |

OTHER PUBLICATIONS

Publication by W. J. Stewart, "A New Technique for Measuring the Refractive Index Profiles of Graded Optical Fibers" 1977, pp. 395–398.
Publication by K. I. White, "The Measurement of the Refractive Index Profiles of Optical Fibers by the Refracted Near Field Technique", pp. 146–155.
Publication by K. I. White, "Practical Application of the Refracted Near-Field Technique for the Measurement of Optical Fiber Refractive Index Profiles", pp. 185–197.
Publication by W. J. Stewart, "Optical Fiber and Preform Profiling Technology", vol. MIT-30, No. 10, Oct. 1982, pp. 1439–1454.

*Primary Examiner*—Vincent P. McGraw
*Attorney, Agent, or Firm*—Richard E. Jenkins

[57] ABSTRACT

A method is disclosed for determining the refractive index profile of an optical fiber wherein light from an intense optical source is focused at the bare fiber end portion of the test fiber. A small amount of light will be coupled into the optical fiber where for the short length of uncoated fiber only cladding modes are excited. The index of refraction is determined directly by analyzing the intensity distribution emitted from the optical fiber with a lens system having a limited numerical aperture.

19 Claims, 4 Drawing Sheets

METHOD OF MEASURING THE REFRACTIVE INDEX PROFILE OF OPTICAL FIBERS

TECHNICAL FIELD

This invention relates generally to a method for testing optical fibers, and particularly to a method for determining the refractive index profile of optical fibers of the type used as telecommunication lightguides.

BACKGROUND ART

Optical fibers are generally constructed with a glass cylindrical core encased within one or more layers of cladding, and light pulses are transmitted through the core of the optical fiber. The light rays or modes of a pulse, typically from a laser diode or light emitting diode, follow different paths within the optical fiber core as they reflect back and forth along the boundary of the core and cladding. Since the pulse length has a tendency to elongate during travel along the core and thereby restrain the bandwidth, optical fibers have been manufactured with their core having an index of refraction profile that varies radially from the axis of the core to the periphery to facilitate telecommunication applications. The refractive index distribution within the optical fiber core should be designed so as to cause all light rays of a pulse to travel along the optical fiber at the same axial velocity regardless of variations in the length of the path traversed. In practice, optical fiber manufacturing processes introduce some deviation from optimum refractive index distribution of the optical fiber core. Therefore, the variation from an optimal refractive index distribution must be consistently monitored to ensure that the variation remains within certain predetermined acceptable limits.

A number of methods have been developed and are known for analyzing the refractive index profile of optical fibers. A good review of the various optical fiber and preform index-profiling methods are disclosed in an article by W. J. Stewart titled "Optical Fiber and Preform Profiling Technology", *IEEE Transactions on Microwave Theory and Techniques,* Vol. MTT-30, No. 10 (October, 1982). Perhaps the most widely accepted method in use today is the refracted near-field method described in the previously noted article. With this particular method a lens having a numerical aperture substantially larger than that of the fiber focuses a beam of light on a flat endface of a fiber and scans the focused spot across the fiber diameter. Part of the light is guided down the fiber while the rest is refracted through an end portion of the fiber and radiates as a hollow cone outside of the fiber. A shield or disc is placed in the radiated cone to prevent the leaky modes in addition to the purely reflected modes from reaching a photodetector which is positioned beyond the disc. A detailed review of this method is set forth in an article titled "Practical Application of the Refracted Near-Field Technique for the Measurment of Optical Fiber Refractive Index Profiles" by K. I. White which was published in the March, 1979 issue of *Optical and Quantum Electronics.*

However, the refracted near-field technique suffers from the practical problem of requiring highly sophisticated optical equipment and thereby renders obtaining refractive index profiles a complex and expensive task. The improved method of the present invention is directed to obviating the requirement for sophisticated optical equipment or complex procedures in order to obtain accurate refractive index profiles of optical fibers.

DISCLOSURE OF THE INVENTION

In accordance with the present invention, a method is provided for determining the refractive index profile of an optical fiber which does not require sophisticated optical equipment or complicated measurement techniques. The method comprises directing light from an intense optical source at the uncoated end portion of an optical fiber, most suitably at the interface of the bare fiber and the coating, in such a fashion that only cladding modes will be excited along the length of the uncoated fiber and the excitation of the cladding modes is uniform. The light emerging from the bare test end of the optical fiber is directed through a lens system which has a selected limited numerical aperture and into a vidicon camera and electrically connected computer. The refractive index profile is then computed from the measured intensity distribution of the light emerging from the test end of the optical fiber.

Therefore, it is an important object of the present invention to provide a method for obtaining the refractive index profile of an optical fiber using relatively simple and unsophisticated optical equipment.

More specifically, an object of the present invention is to provide a method for measuring the refractive index of single mode or multimode optical fibers which does not require sophisticated optical equipment or complex procedures.

Still a further object of the present invention is to provide a method for measuring the refractive index profile of an optical fiber by exciting only cladding modes within the fiber and analyzing the intensity distribution of light emitted from the test fiber with a lens systems whose numerical aperture is limited.

BRIEF DESCRIPTION OF THE DRAWINGS

The present invention will now be described in detail with reference to the accompanying drawings in which.

BEST MODE FOR CARRYING OUT THE INVENTION

Figure 1:
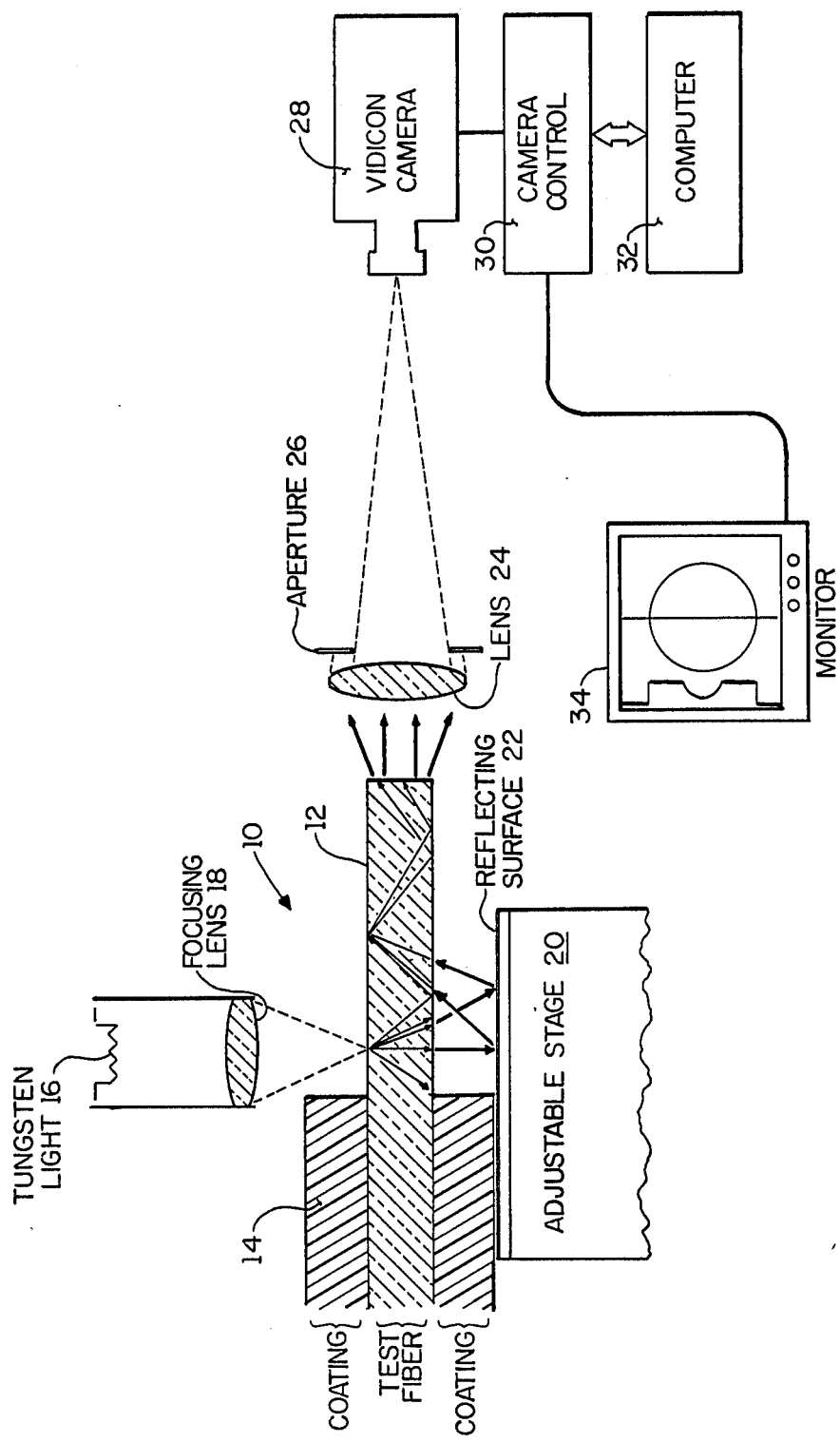
FIG. 1 is a schematic diagram of a system for measuring the index of refraction profile of an optical fiber utilizing the method of the present invention.

Referring now in more detail to the drawings, there is schematically shown in FIG. 1 apparatus for measuring the refractive index profile of an optical fiber 10 comprising bare fiber 12 and coating 14. Bare fiber 12 can be seen with reference to FIGS. 2 and 3 as further comprising an inner core region 11 surrounded by an outer cladding 13. The term "optical fiber" has been used to indicate both single mode and multimode optical fibers.

A tungsten light 16 and focusing lens 18 are used to direct light toward the interface of uncoated optical fiber 12 and coating 14. It should be appreciated that uncoated optical fiber 12 is surrounded by air or any suitable material whose refractive index is less than the refractive index of cladding 13. With this relative positioning of tungsten light 16 and optical fiber 10 a small fraction of the light power will be coupled into cladding 13 where for the short length of uncoated optical fiber 12 only cladding modes will be excited. Optical fiber 10 is positioned on micro-adjustable fiber stage 20 and reflecting material 22 is provided therebetween to enhance the uniformity of the cladding modes excited by tungsten light 16.

The light coupled into bare optical fiber 12 is emitted from the end of the fiber and projected through lens 24 and aperture 26 into vidicon camera 28. Aperture 26 is variable and most suitably placed directly behind lens 24 so as to limit the numerical aperture of the light measurement system. Vidicon camera 28 is electrically connected to camera control 30 and computer 32, and is additionally provided with video monitor 34. Computer 32 is most suitably programmed with software which converts the emitted light intensity distribution from uncoated optical fiber 12 directly into the refractive index profile of the fiber.

Figure 2:
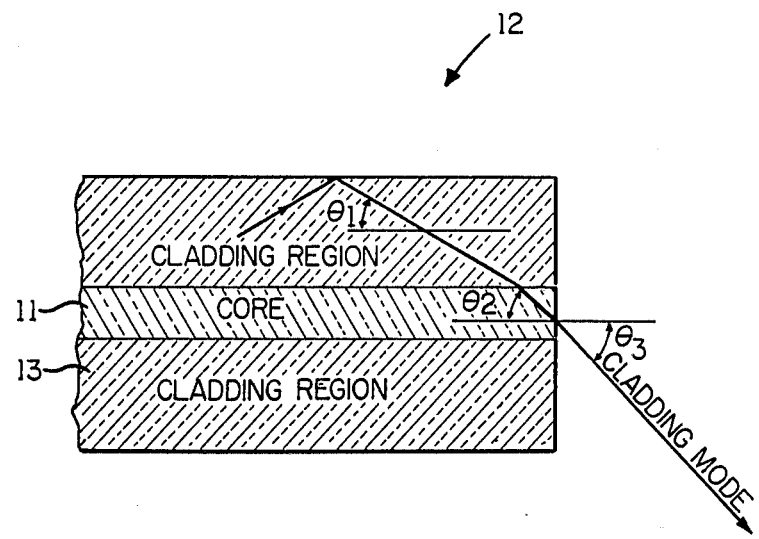
FIG. 2 is a vertical cross-section view of an optical fiber illustrating propagation of a cladding mode through an optical fiber in accordance with the present invention.

In practice, the cladding mode near-field method of the invention is practiced by removing coating 14 from the end of a short portion of optical fiber 10 and preparing the endface for testing according to conventional procedures. The uncoated optical fiber 12 is surrounded with a material such as air whose refractive index is less than the refractive index of cladding 13. The light from tungsten light 16 will excite only cladding modes in optical fiber 12 which will propagate along the uncoated fiber length as best seen in FIG. 2. Utilizing Snell's law, light ray trajectories at the output end of optical fiber 10 can be described by:

$$No \cos \theta_1 = N(r) \cos \theta_2 \quad (1)$$

$$N(r) \sin \theta_2 = \sin \theta_3 \quad (2)$$

where $N(r)$ is the local refractive index along the exit plane of fiber 10 and No is the refractive index of cladding 13. The angle of incidence $\theta_1$ can be uniquely related to the corresponding exit angle $\theta_3$ by combining equations 1 and 2 from above as follows:

$$N(r)^2 - No^2 = -No^2 \sin^2\theta_1 + \sin^2\theta_3 \quad (3)$$

It is apparent from equation three that the magnitude of $N(r)$ at any radial position along the endface of optical fiber 10 determines the relationship between $\theta_1$ and $\theta_3$. Therefore, if No and $\sin \theta_3$ are fixed, a change in $N(r)$ will induce an equivalent change in $\sin \theta_1$.

The emitted intensity distribution from the endface of optical fiber 10 is measured by vidicon camera 28 whose numerical aperture is limited (fixed at $\sin \theta_{3max}$) by placement of a selected optimum aperture 26 behind lens 24 so that the total power at any arbitrary point along the detected pattern is directly related to $\theta_{1max}$ (the power due to the total number of cladding modes propagating with an angle of incidence less than or equal to $\theta_{1max}$). Since the relationship between $\theta_1$ and intensity can be determined prior to conducting refractive index profile measurements by a technique to be described hereafter, then merely by utilizing equation 3, $N(r)$ values can be determined directly from the measured intensity distribution by computer 32. It should be again observed that uniformity of cladding mode excitation by tungsten light 16 is required in order for the above relationship to be valid. This is facilitated by the orientation of tungsten light 16 and focusing lens 18 so as to direct light generally perpendicularly to the longitudinal axis of optical fiber 10. Moreover, microadjustable fiber stage 20 assists in proper alignment of optical fiber 10 relative to tungsten light 16, and reflecting material 22 serves to reflect the light to enhance the uniform launch condition.

Figure 3:
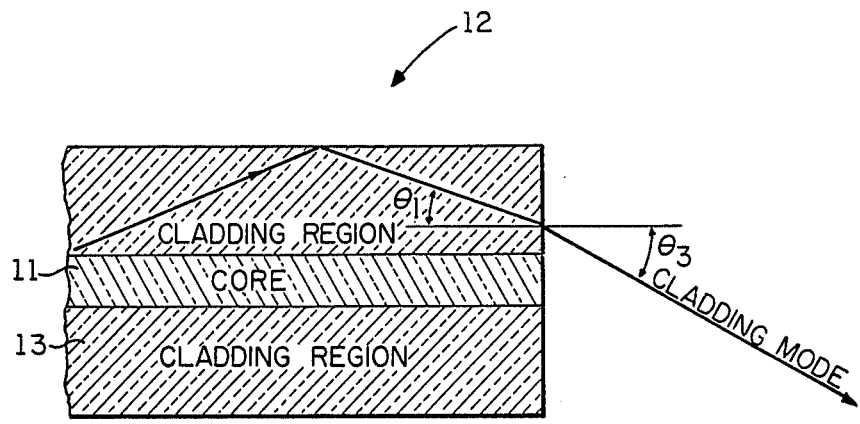
FIG. 3 is a vertical cross-section diagram of an optical fiber illustrating cladding mode propagation used for calibration.
Figure 4:
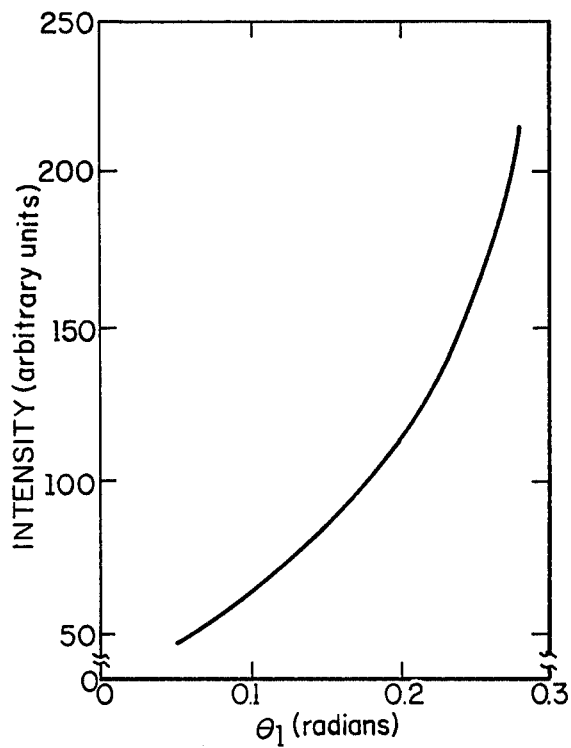
FIG. 4 is a graphic illustration of a typical calibration curve.

Therefore, if uniform cladding mode excitation exists the refractive index profile of optical fiber 10 can be determined by analyzing the emitted intensity distribution. However, for each optical fiber which is analyzed by the cladding near-field method of the present invention, the relationship between intensity and $\theta_1$ (the variable used to calculate the index of refraction) must be determined prior to beginning the measurement by a calibration procedure. Since this relationship may be slightly different for different optical fibers, the calibration procedure should be conducted before each individual fiber refractive index profile measurement. With reference now to FIGS. 3 and 4, applicant will describe the basic principle for the calibration step used to determine the relationship between intensity and $\theta_1$. Applying Snell's law to cladding area 13 only (see FIG. 3), light exiting this area can be described by the following equation which is equation three simplified for the cladding region:

$$\theta_1 = \sin^{-1}(1/No \sin \theta_3) \quad (4)$$

where $\theta_1$ is the cladding mode propagation angle of incidence, $\theta_3$ is the angle at which light exits cladding area 13, and No is the refractive index of cladding 13 and is a constant value. Placing a variable aperture 26 or several different apertures 26 between optical fiber 10 and vidicon camera 28 enables the numerical aperture or light acceptance ability of the light detection system to be adjusted. Since the numerical aperture is $\sin \theta_3$, the relationship between $\theta_1$ and intensity may be easily obtained from the equation by measuring the intensity along cladding 13 for several, most suitably four, different size apertures 26. Fitting this information to a least squares technique provides for plotting a calibration curve such as the representative curve shown in FIG. 4. Then a selected aperture (for best spatial resolution and within the signal to noise ratio of the detector) is used to obtain an intensity profile for fiber 10. Using the previously developed calibration curve to determined $\theta_1$ values corresponding to the intensity values, the necessary $\theta_1$ values are developed to facilitate computation of the refractive index of fiber 10 from equation three by computer 32.

Having explained the theory supporting the method of the present invention, the preferred procedure for calibration and measurement may be very simply set forth. First of all, the endface of optical fiber 10 is prepared for testing according to standard procedures. Optical fiber 10 is inserted into stage 20 and adjusted until maximum alignment is obtained. The intensity profile is observed on monitor 34 to ensure uniform cladding mode excitation which is indicated by a flat intensity profile along the cladding region. A first calibration aperture 26 is placed into position and the intensity level along the cladding region is measured with vidicon camera 28, $\theta_3$ is determined by computer 32 from the aperture size used and $\theta_1$ is calculated by computer 32 using equation four above. The first calibration aperture 26 is removed and a second inserted and the procedure repeated. A third and fourth calibration aperture 26 are used and the process again repeated. Next, using a least squares means technique, the measured intensities and calculated $\theta_{1s}$ are fit to the following equation to plot the calibration curve:

$$I(\theta_1) = A\theta_1^2 + B\theta_1 + C \tag{5}$$

Figure 5:
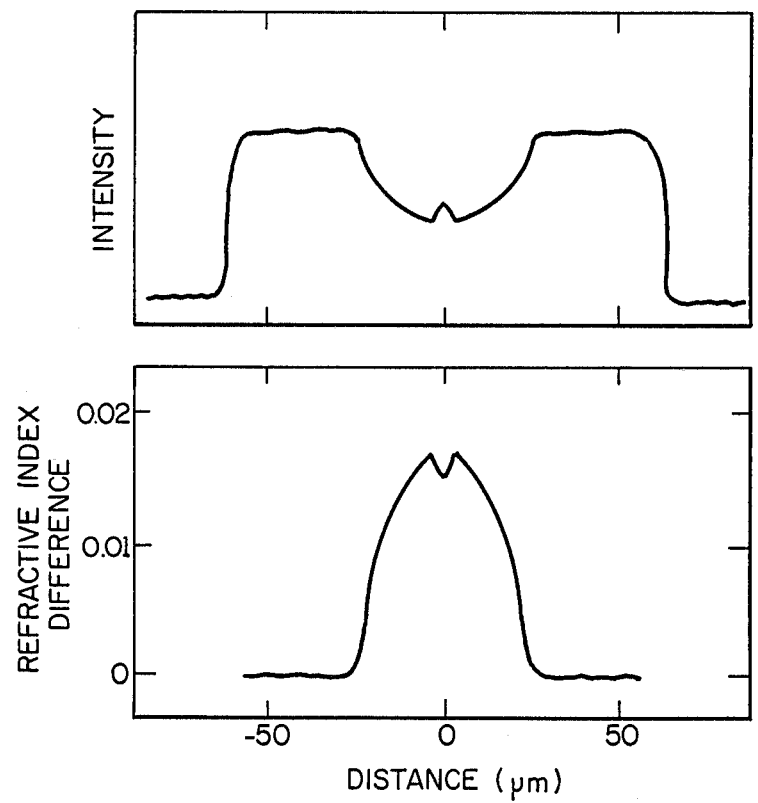
FIG. 5 is a graphical representation of a typical intensity distribution curve and the corresponding refractive index profile obtained using the method of the present invention.

The calibration is now complete and the refractive index profile of optical fiber 10 may now be determined easily by inserting the previously selected optimum measurement aperture 26 and scanning the total intensity profile emitted from optical fiber 10. Utilizing the fitted calibration curve, the measured intensity can be converted into the coinciding refractive index profile by computer 32 using equation three as previously described (see FIG. 5).

Summarily, a new method is provided to measure the refractive index profile of optical fibers which obviates the need for sophisticated light launching equipment and provides greater ease of acquisition of profile measurements since the results are obtained directly from measured intensity distribution.

While the instant invention has been shown and described herein in what is conceived to be the most practical and preferred embodiment, it is recognized that departures may be made therefrom within the scope of the invention which is therefore not to be limited to the details disclosed herein but is to be accorded the full scope of the claims so as to embrace any and all equivalent methods.

What is claimed is:

1. A method of measuring the refractive index profile of an optical fiber comprising a encased within a surrounding cladding and having a protective coating thereover, comprising the steps of:
   providing an uncoated end portion of the optical fiber for testing;
   surrounding at least the uncoated end portion of the optical fiber with a material having a refractive index less than the refractive index of the cladding;
   directing light from an optical source at the uncoated optical fiber so that only cladding modes will be excited along the length of uncoated fiber;
   focusing a limited portion of the light emergent from the test end of the optical fiber into a light detector means which is electrically connected to a computer; and
   computing the refractive index profile of the optical fiber from the measured near field intensity distribution of the light emerging from the test end of the optical fiber.

2. A method according to claim 1 wherein the optical fiber is a single mode fiber.

3. A method according to claim 1 wherein the optical fiber is a multimode fiber.

4. A method according to claim 1 wherein the optical fiber is surrounded by air.

5. A method according to claim 1 wherein the light is directed substantially at the interface of the uncoated optical fiber and the coating and perpendicularly to the longitudinal axis of the optical fiber.

6. A method according to claim 1 wherein the excitation of the cladding modes is uniform.

7. A method according to claim 6 wherein said focusing step includes directing the emergent light into a vidicon camera through a lens systems having a limited numerical aperture.

8. A method according to claim 7 wherein the refractive index profile can be computed from the measured intensity distribution of the light emerging from the test end of the optical fiber according to the relationship $$N(r)^2 - No^2 = -No^2 \sin^2\theta_1 + \sin^2\theta_3$$

where
   $N(r)$ is the local refractive index along the exit plane of the fiber
   $No$ is the refractive index of the cladding
   $\theta_1$ is the cladding mode propagation angle of incidence
   $\theta_3$ is the angle at which light exits the cladding and the numerical aperture of the lens system is fixed at $\sin\theta_{3max}$, $No$ is fixed and the relationship between $\theta_1$ and intensity has been determined.

9. A method according to claim 8 wherein the relationship between $\theta_1$ and intensity for the optical fiber being tested can be computed according to the relationship $$\theta_1 = \sin^{-1}(1/No \sin\theta_3)$$

where $\theta_1$ is the cladding mode propagation angle of incidence, $\theta_3$ is the angle at which light exits the cladding, and $No$ is the constant value refractive index of the cladding.

10. A method of measuring the refractive index profile of an optical fiber after removing coating adjacent the test end of the optical fiber and surrounding at least the test end of the optical fiber with a material having a refractive index less than the refractive index of the cladding comprising the steps of:
   directing light from an intense optical source substantially at the interface of the uncoated optical fiber and the coating so as to excite only cladding modes along the length of uncoated fiber, said cladding modes being uniformly excited by the light;
   focusing a limited portion of the light emergent from the test end of the optical fiber into a vidicon camera having an electrically connected computer, said selected portion determined by a lens system having a limited numerical aperture; and
   computing the refractive index profile of the optical fiber from the measured near-field intensity distribution of the light emerging from the test end of the optical fiber.

11. A method according to claim 10 wherein the optical fiber is a single mode fiber.

12. A method according to claim 10 wherein the optical fiber is a multi-mode fiber.

13. A method according to claim 10 wherein the optical fiber is surrounded by air.

14. A method according to claim 10 wherein the light is directed substantially perpendicularly to the longitudinal axis of the optical fiber.

15. A method according to claim 14 wherein the optical source is a tungsten light source.

16. A method according to claim 10 wherein the refractive index profile can be computed from the measured intensity distribution of the light emerging from the test end of the optical fiber according to the relationship $$N(r)^2 - No^2 = -No^2 \sin^2 \theta_1 + \sin^2 \theta_3$$

where $N(r)$ is the local refractive index along the exit plane of the fiber $No$ is the refractive index of the cladding $\theta_1$ is the cladding mode propagation angle of incidence $\theta_3$ is the angle at which light exits the cladding and the numerical aperture of the lens system is fixed at $\sin \theta_{3max}$, $No$ is fixed and the relationship between $\theta_1$ and intensity has been determined.

17. A method of measuring the refractive index profile of an optical fiber comprising a substantially cylindrical core encased within a surrounding cladding and having a protective coating thereover, comprising the steps of:

providing an uncoated end portion of the optical fiber for testing;

surrounding at least the uncoated end portion of the optical fiber with a material having a refractive index less than the refractive index of the cladding;

directing light from an optical source at the uncoated optical fiber so that only cladding modes will be excited along the length of uncoated fiber and the excitation of the cladding modes is uniform;

focusing a limited portion of the light emergent from the test end of the optical fiber into a vidicon camera through a lens system having a limited numerical aperture, said vidicon camera being electrically connected to a computer; and computing the refractive index profile of the optical fiber from the measured intensity distribution of the light emerging from the test end of the optical fiber according to the relationship $$N(r)^2 - No^2 = -No^2 \sin^2 \theta_1 + \sin^2 \theta_3$$

where $N(r)$ is the local refractive index along the exit plane of the fiber $No$ is the refractive index of the cladding $\theta_1$ is the cladding mode propagation angle of incidence $\theta_3$ is the angle at which light exits the cladding and the numerical aperture of the lens system is fixed at $\sin \theta_{3max}$, $No$ is fixed and the relationship between $\theta_1$ and intensity has been determined.

18. A method of measuring the refractive index profile of an optical fiber comprising a substantially cylindrical core encased within a surrounding cladding and having a protective coating thereover, comprising the steps of:

providing an uncoated end portion of the optical fiber for testing;

surrounding at least the uncoated end portion of the optical fiber with a material having a refractive index less than the refractive index of the cladding;

directing light from an optical source at the uncoated optical fiber so that only cladding modes will be excited along the length of uncoated fiber and the excitation of the cladding modes is uniform;

focusing a limited portion of the light emergent from the test end of the optical fiber into a vidicon camera through a lens system having a limited numerical aperture, said vidicon camera being electrically connected to a computer; and computing the refractive index profile of the optical fiber from the measured intensity distribution of the light emerging from the test end of the optical fiber according to the relationship $$N(r)^2 - No^2 = -No^2 \sin^2 \theta_1 + \sin^2 \theta_3$$

where $N(r)$ is the local refractive index along the exit plane of the fiber $No$ is the refractive index of the cladding $\theta_1$ is the cladding mode propagation angle of incidence $\theta_3$ is the angle at which light exits the cladding and the numerical aperture of the lens system is fixed at $\sin \theta_{3max}$, $No$ is fixed and the relationship between $\theta_1$ and intensity for the optical fiber being tested can be computed according to the relationship $$\theta_1 = \sin^{-1} (1/No \sin \theta_3)$$

where $\theta_1$ is the cladding mode propagation angle of incidence, $\theta_3$ is the angle at which light exits the cladding, and $No$ is the constant value refractive index of the cladding.

19. A method of measuring the refractive index profile of an optical fiber after removing coating adjacent the test end of the optical fiber and surrounding at least the test end of the optical fiber with a material having a refractive index less than the refractive index of the cladding, comprising the steps of:

directing light from an intense optical source substantially at the interface of the uncoated optical fiber and the coating so as to excite only cladding modes along the length of uncoated fiber, said cladding modes being uniformly excited by the light;

focusing a limited portion of the light emergent from the test end of the optical fiber into a vidicon camera having an electrically connected computer, said selected portion determined by a lens system having a limited numerical aperture; and computing the refractive index profile of the optical fiber from the measured intensity distribution of the light emerging from the test end of the optical fiber according to the relationship $$N(r)^2 - No^2 = -No^2 \sin^2 \theta_1 + \sin^2 \theta_3$$

where $N(r)$ is the local refractive index along the exit plane of the fiber $No$ is the refractive index of the cladding $\theta_1$ is the cladding mode propagation angle of incidence $\theta_3$ is the angle at which light exits the cladding and the numerical aperture of the lens system is fixed at $\sin \theta_{3max}$, $No$ is fixed and the relationship between $\theta_1$ and intensity has been determined.

* * * * *

UNITED STATES PATENT AND TRADEMARK OFFICE
CERTIFICATE OF CORRECTION

PATENT NO. : 4,779,978

DATED : October 25, 1988

INVENTOR(S) : Hatton et al.

It is certified that error appears in the above-identified patent and that said Letters Patent is hereby corrected as shown below:

In Column 2, line 37 change "systems" to --system--.

Claim 1, line 2, before "encased" insert --core--.

Signed and Sealed this

Twenty-eighth Day of March, 1989

Attest:

DONALD J. QUIGG

*Attesting Officer*          Commissioner of Patents and Trademarks